US008969302B2

(12) United States Patent
Klinger

(10) Patent No.: US 8,969,302 B2
(45) Date of Patent: *Mar. 3, 2015

(54) LOW FREQUENCY GLATIRAMER ACETATE THERAPY

(71) Applicant: Ety Klinger, Tel Aviv (IL)

(72) Inventor: Ety Klinger, Tel Aviv (IL)

(73) Assignee: Yeda Research & Development Co., Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/770,677

(22) Filed: Feb. 19, 2013

(65) Prior Publication Data

US 2013/0165387 A1 Jun. 27, 2013

Related U.S. Application Data

(63) Continuation of application No. 12/806,684, filed on Aug. 19, 2010, now Pat. No. 8,399,413.

(60) Provisional application No. 61/274,687, filed on Aug. 20, 2009, provisional application No. 61/337,612, filed on Feb. 11, 2010.

(51) Int. Cl.
*A61K 36/00* (2006.01)
*A61K 38/02* (2006.01)
*A61K 38/07* (2006.01)
*A61K 38/16* (2006.01)

(52) U.S. Cl.
CPC ............... *A61K 38/02* (2013.01); *A61K 38/07* (2013.01); *A61K 38/16* (2013.01)
USPC .......................................... 514/17.9; 514/1.1

(58) Field of Classification Search
None
See application file for complete search history.

(56) References Cited

U.S. PATENT DOCUMENTS

| | | | |
|---|---|---|---|
| 3,849,550 A | 11/1974 | Teitelbaum et al. |
| 5,800,808 A | 9/1998 | Konfino et al. |
| 5,981,589 A | 11/1999 | Konfino et al. |
| 6,048,898 A | 4/2000 | Konfino et al. |
| 6,054,430 A | 4/2000 | Konfino et al. |
| 6,214,791 B1 | 4/2001 | Arnon et al. |
| 6,342,476 B1 | 1/2002 | Konfino et al. |
| 6,362,161 B1 | 3/2002 | Konfino et al. |
| 6,514,938 B1 | 2/2003 | Gad et al. |
| 6,620,847 B2 | 9/2003 | Konfino et al. |
| 6,800,285 B2 | 10/2004 | Rodriguez et al. |
| 6,800,287 B2 | 10/2004 | Gad et al. |
| 6,844,314 B2 | 1/2005 | Eisenbach-Schwartz et al. |
| 6,939,539 B2 | 9/2005 | Konfino et al. |
| 7,022,663 B2 | 4/2006 | Gilbert et al. |
| 7,033,582 B2 | 4/2006 | Yong et al. |
| 7,074,580 B2 | 7/2006 | Gad et al. |
| 7,163,802 B2 | 1/2007 | Gad et al. |
| 7,199,098 B2 | 4/2007 | Konfino et al. |
| 7,279,172 B2 | 10/2007 | Aharoni et al. |
| 7,425,332 B2 | 9/2008 | Aharoni et al. |
| 7,429,374 B2 | 9/2008 | Klinger |
| 7,495,072 B2 | 2/2009 | Dolitzky |
| 7,560,100 B2 | 7/2009 | Pinchasi et al. |
| 7,615,359 B2 | 11/2009 | Gad et al. |
| 7,625,861 B2 | 12/2009 | Konfino et al. |
| 7,855,176 B1 | 12/2010 | Altman et al. |
| 7,923,215 B2 | 4/2011 | Klinger |
| 7,928,131 B2 | 4/2011 | Buzard et al. |
| 8,232,250 B2 | 7/2012 | Klinger |
| 8,399,413 B2 | 3/2013 | Klinger |
| 8,709,433 B2 | 4/2014 | Kasper et al. |
| 8,759,302 B2 | 6/2014 | Dhib-Jalbut et al. |
| 2002/0037848 A1 | 3/2002 | Eisenbach-Schwartz et al. |
| 2002/0077278 A1 | 6/2002 | Yong et al. |
| 2004/0106554 A1 | 6/2004 | Konfino et al. |
| 2005/0014694 A1 | 1/2005 | Yong et al. |
| 2005/0019322 A1 | 1/2005 | Rodriguez et al. |
| 2005/0170004 A1 | 8/2005 | Rosenberger |
| 2005/0171286 A1 | 8/2005 | Konfino et al. |
| 2006/0154862 A1 | 7/2006 | Ray et al. |
| 2006/0172942 A1 | 8/2006 | Dolitzky |
| 2006/0189527 A1 | 8/2006 | Rasmussen et al. |
| 2006/0194725 A1 | 8/2006 | Rasmussen et al. |

(Continued)

FOREIGN PATENT DOCUMENTS

WO WO00/18794 4/2000
WO WO 00/20010 4/2000

(Continued)

OTHER PUBLICATIONS

Flechter et al., Copolymer 1 (Glatiramer Acetate) in Relapsing Forms of Multiple Sclerosis: Open Multicenter Study of Alternate-Day Administration, Jan.-Feb. 2002, Clinical Neuropharmacology 25(1);11-15.*
U.S. Appl. No. 12/861,655, filed Aug. 23, 2010, Stark et al.
U.S. Appl. No. 12/231,292, filed Aug. 29, 2008, Aharoni et al.
U.S. Appl. No. 12/761,367, filed Apr. 15, 2010, Altman et al.
U.S. Appl. No. 12/785,125, filed May 21, 2010, Altman et al.
U.S. Appl. No. 13/384,021, filed Jul. 14, 2010, Altman et al.
U.S. Appl. No. 13/083,112, filed Apr. 8, 2011, Klinger.
U.S. Appl. No. 11/651,212, filed Jan. 9, 2007, Pinchasi.
U.S. Appl. No. 12/806,684, filed Aug. 19, 2010, Klinger.

(Continued)

*Primary Examiner* — John Ulm
(74) *Attorney, Agent, or Firm* — John P. White; Gary J. Gershik; Cooper & Dunham LLP

(57) ABSTRACT

A method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

12 Claims, No Drawings

(56) References Cited

U.S. PATENT DOCUMENTS

| | | |
|---|---|---|
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0037740 A1 | 2/2007 | Pinchasi et al. |
| 2007/0048794 A1 | 3/2007 | Gad et al. |
| 2007/0054857 A1 | 3/2007 | Pinchasi et al. |
| 2007/0059798 A1 | 3/2007 | Gad |
| 2007/0161566 A1 | 7/2007 | Pinchasi |
| 2007/0173442 A1 | 7/2007 | Vollmer |
| 2009/0048181 A1 | 2/2009 | Schipper et al. |
| 2009/0053253 A1 | 2/2009 | Klinger |
| 2009/0149541 A1 | 6/2009 | Stark et al. |
| 2010/0167983 A1 | 7/2010 | Kreitman et al. |
| 2010/0210817 A1 | 8/2010 | Gad et al. |
| 2010/0285600 A1 | 11/2010 | Lancet et al. |
| 2011/0066112 A1 | 3/2011 | Altman et al. |

FOREIGN PATENT DOCUMENTS

| | | |
|---|---|---|
| WO | WO 00/27417 | 5/2000 |
| WO | WO 2004/043995 | 5/2004 |
| WO | WO 2004/064717 | 8/2004 |
| WO | WO 2004/091573 A1 | 10/2004 |
| WO | WO 2005/041933 | 5/2005 |
| WO | WO2005/120542 | 12/2005 |
| WO | WO 2006/029036 A2 | 3/2006 |
| WO | WO 2006/050122 | 5/2006 |
| WO | WO 2007/081975 | 7/2007 |
| WO | WO 2007/081975 A1 | 7/2007 |
| WO | WO 2008/006026 | 1/2008 |
| WO | WO 2009/070298 | 6/2009 |
| WO | WO 2011/008274 A2 | 1/2011 |
| WO | WO2011/022063 | 2/2011 |

OTHER PUBLICATIONS

International Search Report issued Oct. 4, 2010 in connection with PCT International Application No. PCT/US10/02283, filed Aug. 19, 2010 (Klinger).

Written Opinion of the International Searching Authority issued Oct. 4, 2010 in connection with PCT International Application No. PCT/US10/02283, filed Aug. 19, 2010 (Klinger).

Anderson, et al. (1992) "Revised estimate of the prevalence of multiple sclerosis in the United States". Ann Neurol. 31:333-36.

Anderson, et al. "Injection pain decreases . . . " The Consortium of Multiple Sclerosis Centers 2010 Annual Meeting, Jun. 2-5, 2010, San Antoinio, Texas (Abstract only).

Arnon and Aharoni (2007) "Neurogenesis and neuroprotection in the CAN—Fundamental elements in the effect of . . . ". Mol Neurobiol. 36:245-53.

Bjartmar C, et al. (2002) "Pathological mechanisms and disease progression of multiple sclerosis: therapeutic implications". Drugs of Today. 38:7-29.

Bornstein, et al., "Treatments of Multiple Sclerosis with a Synthetic Polypeptide: Preliminary Results," Ann. Neurol., 1980, 8, 117 (Abstract).

Bornstein, et al., "Treatments of Multiple Sclerosis with a Synthetic Polypeptide: Preliminary Results," Trans. Am. Neurol. Assoc., 1980, 105, 348-350.

Bornstein, et al., "Multiple Sclerosis: Trial of a Synthetic Polypeptide," Ann. Neurol., 1982, 11, 317-319.

Bornstein, et al., "Clinical Trials of Copolymer 1 in Multiple Sclerosis," Ann. N.Y. Acad. Sci. (USA), 1984, 366-372.

Bornstein, et al., "Clinical Trials of a Synthetic Polypeptide (Copolymer 1) for the treatment of Mutliple Sclerosis" in Gonsett et al., Immunological and Clinical Aspects of Multiple Sclerosis (MTP Press, The Hague, 1984) 144-150.

Bornstein, et al., "Multiple Sclerosis: Clinical Trials of a Synthetic Polypeptide, Copolymer 1," Neurol., 1985, 35, (Suppl. 1), 103 (Abstract).

Bornstein, "Cop 1 may be Beneficial for Patients with Exacerbating-remitting Form of Multiple Sclerosis," Adv. Ther. (USA), 1987, 4, 206 (Abstract) (Exhibit 45).

Bornstein, et al., "A Pilot Trial of Cop 1 in Exacerbating-remitting Multiple Sclerosis," New Eng. J. Med., 1987, 317(7), 408-414.

Bornstein, et al., "Clinical Experience with COP-1 in Multiple Sclerosis," Neurol., 1988, 38(Suppl. 2) 66-69.

Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].

Bornstein, et al., "Pilot Trial of COP-1 in Chronic Progressive Multiple Sclerosis: Preliminary Report," from the International Multiple Sclerosis Conference: An Update on Multiple Sclerosis, Roma (Italy), Sep. 15-17, 1988, in Elsevier Science Publisher, 1989, 225-232.

Bornstein, et. al., "Clinical Trials of Cop 1 in Multiple Sclerosis," in Handbook of Multiple Sclerosis (S.D. Cook Marcel Rekker, ed., 1990) 469-480.

Bornstein , et al., "A Placebo-controlled, Double-blind, Randomized Two-center, Pilot Trial of Cop 1 in Chronic Prgressive Multiple Sclerosis," Neurol., 1991, 41, 533-539.

Bornstein, et al., "Treatment of Multiple Sclerosis with Copolymer 1" in Treatment of Multiple Sclerosis: Trial Design, Reslts and Future Perspectives (Rudick R.A. & Goodkin D.E., eds., Springder Lerlag, London, 1992) 173-198.

Bornstein, "Clincal Experience: Hopeful Prospects in Multiple Sclerosis," Hospital Practice (Off. Ed.), 1992, vol. 27, No. 5, p. L135-L158, 141-142, 145-158.

Brazeau GA, et al. (1998) "Current perspectives on pain upon injection of drugs". J Pharmaceutical Sci. (87)6:667-677.

Chantelau e, et al. (1991) "What make insulin injections painful?" BMJ. 303:26-27.

Comi, et al. (2008) "Results from a phase III, one-year, randomized, double-blind, parallel-group . . . ". Mult Scler. 14 (suppl 1):S299

Comi G. "Treatment with glatiramer . . . ". Program and abstracts of the American Academy of Neurology 60th Annual Meeting; Apr. 12-19, 2008; Chicago, Illinois. LBS.003.

Comi, et al. (2001) "European/Canadian multicenter, double-blind, randomized, placebo-controlled study . . . ". Ann Neurol. 49:290-7.

Dhib-Jalbut S. (2003) "Glatiramer acetate (Copaxone) therapy for multiple sclerosis" Pharmacology & Therapeutics. 98:245-55.

Dhib-Jalbut S. (2002) "Mechanisms of action of interferons and glatiramer acetate in multiple sclerosis". Neurology. 58(Suppl 4):S3-S9.

Frenken LA, et al. (1994) "Analysis of the efficacy of measures to reduce pain after subcutaneous administration of epoetin alfa". Nephrol Dial Transplant. 9:1295-1298.

Johnson, et al. (1998) "Extended use of glatiramer acetate (Copaxone) is well tolerated . . . ". Neurology. 50:701-8.

Kansara, et al. (2009) "Subcutaneous Delivery". Drug Deliv Technol. Jun. 2009; 9(6):38-42.

Miller D, et al. (2005) "Clinically isolated syndromes suggestive of multiple sclerosis, part I: natural history . . . ". Lancet Neurol. 4(5):281-288.

Miller D, et al. (2005) "Clinically isolated syndromes suggestive of multiple sclerosis, part II: non-conventional MRI . . . ". Lancet Neurol. 4(6):341-348.

Neuhaus O, et al. (2003) "Immunomodulation in multiple sclerosis: from immunosuppression to neuroprotection". Trends Pharmacol Sci. 24:131-138.

Noseworthy, et al. (2000) "Multiple sclerosis". N Engl J Med. 343:938-52.

Polman, et al. (2005) "Diagnostic Criteria for Multiple Sclerosis: 2005 Revisions to the "McDonald" Criteria". Ann Neurol. 58:840-846.

Ruggiere, et al. (2007) "Glatiramer acetate in multiple sclerosis: A review". CNS Drug Reviews. 13(2):178-91.

Schrempf W, et al. (2007) "Glatiramer acetate: Mechanisms of action in multiple sclerosis". Autoimmunity Reviews 2007. 6:469-475.

Shire, et al. (2004) "Challenges in the Development of High Protein Concentration Formulations". J Pharm Sci. 93(6):1390-1402.

Thrower BW. (2007) "Clinically isolated syndromes. Predicting and delaying multiple sclerosis". Neurology. 68 (Suppl 4):S12-S15.

(56) References Cited

OTHER PUBLICATIONS

Tselis, et al. (2007) "Glatiramer acetate in the treatment of multiple sclerosis". Neuropsychiatric Dis Treat. 3(2):259-67.
Weber, et al. (2007) "Mechanism of action of glatiramer acetate treatment of multiple sclerosis". Neurotherapeutics. 4(4):647-53.
Wolinsky J.S. (2006) "The use of a glatiramer acetate in the treatment of multiple sclerosis" Advances in Neurology 98: 273-292.
Wolinsky, JS (2006) "The use of glatiramer acetate in the treatment of multiple sclerosis". Adv Neurol. 273-92.
Van Metre TE, et al. (1996) "Pain and dermal reaction caused by injection glycerin in immunotherapy solutions". J Allergy Clin Immunol. 97:1033-9.
Ziemssen and Schrempf (2007) "Glatiramer acetate: Mechanisms of action in multiple sclerosis". International Rev of Neurobiol. 79:537-70.
Guideline on clinical investigation of medicinal products for the treatment of multiple sclerosis EMEA, London Nov. 16, 2006 CPMP/EWP/561/98 REV.1.
Product Monograph, Copaxone, Revised Apr. 2, 2010: 1-35.
The National MS Society (USA) [cited Feb. 5, 2010]. Available from: www.nationalmssociety.org/about-multiple-sclerosis/what-we-know-about-ms/treatments/index.aspx.
Medical News Today. Jul. 8, 2008. Web: Sep. 9, 2010. www.medicalnewstoday.com/articles/114183.php.
Office Action issued Jul. 20, 2009 in connection with U.S. Appl. No. 11/651,212, filed Jan. 9, 2007.
Amendment filed Jul. 1, 2009 in connection with U.S. Appl. No. 11/651,212, filed Jan. 9, 2007.
Office Action issued Apr. 2, 2009 in connection with U.S. Appl. No. 11/651,212, filed Jan. 9, 2007.
Amendment filed Dec. 22, 2008 in connection with U.S. Appl. No. 11/651,212, filed Jan. 9, 2007.
Office Action issued Jun. 20, 2008 in connection with U.S. Appl. No. 11/651,212, filed Jan. 9, 2007.
Response filed Sep. 23, 2010 in connection with U.S. Appl. No. 12/785,125, filed May 21, 2010.
Office Action issued Aug. 24, 2010 in connection with U.S. Appl. No. 12/785,125, filed May 21, 2010.
Communication issued Jul. 29, 2010 in connection with EPO Application No. 10160099.7.
Response filed Dec. 17, 2010 in connection with European Patent Application No. 10160099.7.
Communication Pursuant to Article 94(3) EPC issued Feb. 11, 2011 in connection with European Patent Application No. 10160099.7.
Response filed Jun. 13, 2011 in connection with European Patent Application No. 10160099.7.
Written Opinion of the International Searching Authority issued Oct. 5, 2007 in connection with PCT International Application No. PCT/US07/00575, filed Jan. 9, 2007.
PCT International Search Report issued Oct. 5, 2007 in connection with PCT International Application No. PCT/US07/00575, filed Jan. 9, 2007.
Written Opinion of the International Searching Authority issued Jun. 9, 2011, in connection with PCT International Application No. PCT/US2010/001972, filed Jul. 14, 2010.
PCT International Search Report issued Jun. 9, 2011 in connection with PCT International Application No. PCT/US2010/001972, filed Jul. 14, 2010.
Polin. The Ins and Outs of Prefilled Syringes. May 2003, Pharmaceutical & Medical Packaging News/Medical Device Link.
Jorgensen J.T. et al. (1996) "Pain assessment of subcutaneous injections" Annals of Pharmacotherapy, Harvey Whitney Books Company, vol. 30. No. 7-8, pp. 729-732.
Feb. 14, 2012 Office Action Issued in Connection With U.S. Appl. No. 13/308,299, filed Nov. 30, 2011 (Klinger).
Amendment in Response to Feb. 14, 2012 Office Action filed May 14, 2012 in connection with U.S. Appl. No. 13/308,299, filed Nov. 30, 2011 (Klinger).
Feb. 29, 2012 Official Action Issued in connection with Canadian Application No. 2,760,802, filed Aug. 19, 2012 (Klinger).
Response to the Feb. 29, 2012 outstanding Examiner's Report filed May 29, 2012 in connection with Canadian Application No. 2,760,802, filed Aug. 19, 2012 (Klinger).
Supplementary European Search Report issued Jul. 13, 2012 in connection with European Patent Application No. 10810282.3 filed Oct. 11, 2011.
Flechter S. et al. (2002) "Comparison of glatiramer acetate (Copaxone(R)) and interferon beta-1b (Betaferon(R)) in multiple sclerosis patients: An open-label 2-year follow up" Journal of the Neurological Sciences vol. 197, No. 1-2 pp. 51-55.
Khan et al. (2008) "Randomized, prospective, rater-blinded, four-year, pilot study to compare the effect of daily versus every-other-day injections in relapsing-remitting multiple" Mult. Scler. 14 Suppl. 1 S296.
Caon Christina et al. (2009) "Randomized, prospective, rater-blinded, four year pilot study to compare the effect of daily versus every other day glatiramer acetate 20 mg subcutaneous injections in RRMS" Neurology vol. 72, No. 11, p. A317.
Simpson Dene et al. (2002) "Glatiramer acetate: A review of its use in relapsing-remitting multiple sclerosis" CNS Drugs vol. 16, No. 12 pp. 825-850.
Official Action issued Nov. 28, 2012 in connection with Eurasian patent application No. 201270292 including English translation thereof.
Preliminary Conclusion of Substantive Examination issued Nov. 8, 2012 in connection with Ukrainian patent application No. 201203259 including English translation thereof.
Examination Report issued Nov. 5, 2012 in connection with New Zealand patent application No. 598661.
Response to the Nov. 25, 2011 Examiner's Report filed Oct. 15, 2012 in Connection With Australian Application No. 2010284666, filed Aug. 19, 2012.
Response to the Jul. 24, 2012 outstanding Examiner's Report filed Oct. 24, 2012 in connection with Canadian Application No. 2,760,802, filed Aug. 19, 2012.
Jul. 24, 2012 Official Action Issued in Connection With Canadian Application No. 2,760,802, filed Aug. 19, 2012.
Communication Pursuant to Article 94(3) EPC issued Aug. 8, 2012 in connection with European Patent Application No. 10810282.3 filed Oct. 11, 2011.
Response to Aug. 8, 2012 Communication Pursuant to Article 94(3) EPC filed Sep. 13, 2012 in connection with European Patent Application No. 10810282.3 filed Oct. 11, 2011.
Feb. 6, 2012 Office Action Issued in Connection With U.S. Appl. 12/806,684, filed Aug. 19, 2010.
Oct. 10, 2012 Office Action Issued in Connection With U.S. Appl. No. 12/806,684, filed Aug. 19, 2010.
Response to the Oct. 10, 2012 Office Action filed Jan. 10, 2013 in connection with U.S. Appl. No. 12/806,684, filed Aug. 19, 2010.
January 17, 2013 Notice of Allowance issued in connection with U.S. Appl. No. 12/806,684, filed Aug. 19, 2010.
Issue Notification issued Feb. 27, 2013 in connection with U.S. Appl. No. 12/806,684, filed Aug. 19, 2010.
Notice of Allowance issued Jun. 15, 2012 issued in Connection With U.S. Appl. No. 13/308,299, filed Nov. 30, 2011.
Issue Notification issued Jul. 11, 2012 issued in Connection With U.S. Appl. No. 13/308,299, filed Nov. 30, 2011.
Feb. 6, 2014 Opposition in connection with European Application No. 10810282.3; Patentee: *Yeda Research and Development Co., Ltd.* vs. Opponent: *Synthon BV.*
Feb. 7, 2014 Opposition in connection with European Application No. 10810282.3; Patentee: *Yeda Research and Development Co., Ltd.* vs, Opponent: *Aetavis Group ehf.*
Feb. 10, 2014 Opposition in connection with European Patent EP2405749 B1.
Feb. 6, 2012 Office Action Issued in Connection With U.S. Appl. No. 12/806,684, filed Aug. 19, 2010 (Klinger).
Jun. 26, 2014 Summons to attend oral proceedings pursuant to Rule 115 (1) EPC in connection with European Patent Application No. 10160099.7.
Nov. 25, 2011 Examiner's Report Issued in Connection With Australian Application No. 2010284666, filed Aug. 19, 2012 (Klinger).

(56) References Cited

OTHER PUBLICATIONS

Response to the Nov. 25, 2011 Examiner's Report filed Oct. 15, 2012 in Connection With Australian Application No. 2010284666, filed Aug. 19, 2012 (Klinger).
Jul. 10, 2013 Official Action Issued in Connection With Canadian Application No. 2,760,802, filed Aug. 19, 2012 (Klinger).
Response to the Jul. 10, 2013 outstanding Examiner's Report filed Oct. 10, 2013 in connection with Canadian Application No. 2,760,802, filed Aug. 19, 2012 (Klinger).
Jan. 8, 2014 Official Action Issued in Connection With Canadian Application No. 2,760,802, filed Aug. 19, 2012 (Klinger).
Response to the Jan. 8, 2014 outstanding Examiner's Report filed Apr. 8, 2014 in connection with Canadian Application No. 2,760,802, filed Aug. 19, 2012 (Klinger).
Apr. 1, 2013 Official Action Issued in Connection With Chinese Application No. 201080036966.0, filed Feb. 20, 2012 (Klinger) and English Translation thereof.
Response to the Apr. 1, 2013 outstanding Official Action filed Jun. 28, 2013 in Connection With Chinese Application No. 201080036966.0, Feb. 20, 2012 (Klinger).
Aug. 9, 2013 Official Action Issued in Connection With Chinese Application No. 201080036966.0, filed Feb. 20, 2012 (Klinger) and English Translation thereof.
Response to the Aug. 9, 2013 outstanding Official Action filed Oct. 24, 2013 in Connection With Chinese Application No. 201080036966.0, Feb. 20, 2012 (Klinger).
Decision of Rejection Issued in Connection With Chinese Application No. 201080036966.0, issued Feb. 8, 2014 (Klinger) and English Translation thereof.
Response to the Nov. 28, 2012 outstanding Official Action in connection with Eurasian patent application No. 201270292 (Klinger).
Official Action issued Mar. 18, 2013 in connection with Eurasian patent application No. 201270292 including English translation thereof.
Response to the Mar. 18, 2013 outstanding Official Action in connection with Eurasian patent application No. 201270292 (Klinger).
Official Action issued Aug. 14, 2013 in connection with Eurasian patent application No. 201270292.
Response to the Aug. 14, 2013 outstanding Official Action in connection with Eurasian patent application No. 201270292 (Klinger).
Jul. 1, 2009 Response to Final Office action in connection with U.S. Appl. No. 11/651,212.
Sep. 13, 2012 Response to Communication under Art 94 (3) EPC in connection with European Application No. 10810282.3.
Communication Pursuant to Rule 69 EPC issued Sep. 2, 2013 in connection with European Patent Application No. 13166080.5.
Extended European Search Report issued Jul. 30, 2013 in connection with European Patent Application No. 13166080.5.
Feb. 26, 2014 Response to Extended European Search Report issued Jul. 30, 2013 in connection with European Patent Application No. 13166080.5.
Jan. 7, 2014 Official Action Issued in Connection With Japanese Application No. 2012-525530, filed Feb. 20, 2012 including English translation thereof.
Sep. 17, 2013 Official Action Issued in Connection with Korean Application No. 10-2012-7007115.
Feb. 5, 2014 Decision of Rejection issued in Connection with Korean Application No. 10-2012-7007115.
Feb. 26, 2014 Office action Issued in Connection With Taiwanese Application No. 099128023, filed Aug. 20, 2010 including English translation thereof.
Preliminary Conclusion of Substantive Examination issued Nov. 8, 2012 in connection with Ukrainian patent application No. 2012 03259 including English translation thereof.
Flechter S, et al. (2002) "Copolymer 1 (Glatiramer Acetate) in Relapsing Forms of Multiple Sclerosis: Open Multicenter Study of Alternate-Day Adlninistration". Clinical Neuropharmacology, 25: 11-15.
Khan O. et al., "A phase 3 trial to assess the efficacy and safety of glatiramer acetate injections 40mg administered 3 times a week compared to placebo" Oct. 13, 2012; European Committee for Treatment and Research in Multiple Sclerosis.
Cohen et al. (2007) "Randomized, double-blind, dose comparison study of glatiramer acetate in relapsing-remitting MS". Neurology, 68: 939-944.
Endo et al. (2004) "How to proceed with therapy of multiple sclerosis". Modern Physician, 24: 1896-1901 including English translation thereof.
Oct. 10, 2012 Media communication by Teva Pharmaceutical Industries Ltd.
Jul. 7, 2008 Trial Update by Teva Pharmaceutical Industries Ltd.
Copaxone 20 mg/ml, Solution for Injection, Pre-Filled Syringe, Summary of Product Characteristics updated on Apr. 17, 2009.
Copaxone 20 mg/ml or Copaxone 40 mg/ml, NDA 020622/S-089 FDA Approved Labeling Text dated Jan. 28, 2014.
Sep. 10, 2014 Complaint, filed in connection with *Teva Pharmaceuticals USA, Inc., et al. v. Sandoz Inc. and Momenta Pharmaceuticals, Inc.* in the United States District Court for the District of Delaware (Case No. 1:14-cv-001171-GMS).
Nov. 3, 2014 Answer, filed in connection with *Teva Pharmaceuticals USA, Inc., et al. v. Sandoz Inc. and Momenta Pharmaceuticals, Inc.* in the United States District Cort for the District of Delaware (Case No. 1:14-cv-001171-GMS).
Sep. 10, 2014 Complaint, filed in connection with *Teva Pharmaceuticals USA, Inc., et al. v. Doctor Reddy's Laboratories Ltd. and Doctor Reddy's Laboratories, Inc.* in the United States District Court for the District of Delaware (Case No. 1:14-cv-01172-GMS).
Nov. 3, 2014 Answer, filed in connection with *Teva Pharmaceuticals USA, Inc., et al. v. Doctor Reddy's Laboratories Ltd. and Doctor Reddy's Laboratories, Inc.* in the United States District Court for the District of Delaware (Case No. 1:14-cv-01172-GMS).
Sep. 11, 2014 Complaint, filed in connection with *Teva Pharmaceuticals USA, Inc., et al. v. Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).
Oct. 6, 2014 Complaint, filed in connection with *Teva Pharmaceuticals USA, Inc., et al. v. Mylan Pharmaceuticals Inc., Mylan Inc. and Natco Pharma Ltd.* in the United States District Court for the District of Delaware (Case No. 1:14-cv-01278-GMS).
Oct. 7, 2014 Complaint, filed in connection with *Teva Pharmaceuticals USA, Inc., et al. v. Mylan Pharmaceuticals Inc., Mylan Inc. and Natco Pharma Ltd.* in the United States District Court for Northern District of West Virginia (Case No. 1:14-cv-00167-IMK).
Nov. 18, 2014 Complaint, filed in connection with *Teva PhaLmaceuticals USA, Inc., et al. v. Synthon Pharmaceuticals Inc., et al.* in the United States District Court for District of Delaware (Case. No. 1:14-cv-01419-UNA).
Nov. 19, 2014 Complaint, filed in connection with *Teva Pharmaceuticals USA, Inc., et al. v. Synthon Pharmaceuticals Inc., et al.* in the United States District Court for Middle District of North Carolina (Case. No. 1:14-cv-975).
Nov. 25, 2014 Plaintiff's Notice of Voluntary Dismissal, filed in connection with *Teva Pharmaceuticals USA, Inc., et al. v. Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).
Costello, K., et al., "Recognizing Nonadherence in Patients with Multiple Sclerosis and Maintaining Treatment Adherence in the Long Term," Medscape J Med., vol. 10(9):225 (2008).
Edgar, C.M., at al., "Lipoatrophy in Patients with Multiple Sclerosis on Glatiramer Acetate," Can. J. Neurol. Sci., vol. 31:58-63 (2004).
Ford, CC., et al. "A Prospective open-label study of glatiramer acetate: over a decade of continuous use in multiple sclerosis patients," Multiple Sclerosis, vol. 12:309-320 (2006).
Gagnon, L., "Every-Other-Day Dosing of Glatiramer Acetate Reduces Adverse Reactions With Comparable Efficacy to Daily Dosing: Presented at WCTRMS," PeerView Press, (Sep. 21, 2008).
Ge, Y., et al. "Glatiramer Acetate (Copaxone) Treatment in Relapsing-Remitting Multiple Sclerosis", Neurology, vol. 54:813-817 (Feb. 2000).

(56) References Cited

OTHER PUBLICATIONS

Johnson, K.P., et al., "Copolymer 1 reduces relapse rate and improves disability in relapsing-remitting multiple sclerosis: Results of a phase III multicenter, double-blind, placebo-controlled trial," Neurology, vol. 45:1268-1276 (Jul. 1995).

Klauer, T., and Zettl, U.K., "Compliance, adherence, and the treatment of multiple sclerosis," J Neurol. vol. 255 (Suppl. 6):87-92 (2008).

Lisak, R.P. and Kira, J., "Chapter 100, Multiple Sclerosis," International Neurology, 366-374 (2009).

Manso, P.J., and Sokol, A.L., "Life cycle management of ageing pharmaceutical assets," Pharmaceutical Law Insight, vol. 3(7):16-19 (Jul./Aug. 2007).

A Study to Test the Effectiveness and Safety of a New Higher 40mg Dose of Copaxone® Compared to Copaxone® 20mg, the Currently Approved Dose [online]. ClinicalTrials.gov, 1993 [retrieved on Sep. 3, 2014]. Retrieved from the Internet: <URL: clinicaltrials.gov/show/NCT00202982>.

Copaxone®, Physicians' Desk Reference, 62nd ed. Montvale, NJ, Thomson Healthcare Inc., pp. 3231-3235 (2008).

Rebif® (interferon beta-1a), Product Description, 103795.5062PI final Jun. 7, 2005.

This Is MS Multiple Sclerosis Community: Knowledge & Support [online]. ThisIsMS [retrieved on Sep. 3, 2014]. Retrieved from the Internet: <URL:www.thisisms.com/forum/copaxonef4/topic5610.html>.

Immunological Responses to Different Doses of Glatiramer Acetate in MS: Analyses from the FORTE Trial, Yong W. V., et al., poster session dated Apr. 28, 2009, presented at the 61st Annual American Academy of Neurology meeting in Seattle, Washington U.S.A.

\* cited by examiner

LOW FREQUENCY GLATIRAMER ACETATE THERAPY

This application is a continuation of U.S. Ser. No. 12/806,684, filed Aug. 19, 2010, now allowed, which claims the benefit of U.S. Provisional Applications Nos. 61/337,612, filed Feb. 11, 2010 and 61/274,687, filed Aug. 20, 2009, the contents of all of which are hereby incorporated by reference in their entirety.

Throughout this application various publications are referenced by their full citations. The disclosures of these publications in their entireties are hereby incorporated by reference into this application in order to more fully describe the state of the art to which this invention pertains.

BACKGROUND OF THE INVENTION

Multiple Sclerosis (MS) is a chronic, debilitating disease of the central nervous system (CNS). MS has also been classified as an autoimmune disease. MS disease activity can be monitored by magnetic resonance imaging (MRI) of the brain, accumulation of disability, as well as rate and severity of relapses.

There are five main forms of multiple sclerosis:
1) Benign Multiple Sclerosis:
Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

2) Relapsing-Remitting Multiple Sclerosis (RRMS):
Patients suffering from RRMS experience sporadic exacerbations or relapses, as well as periods of remission. Lesions and evidence of axonal loss may or may not be visible on MRI for patients with RRMS.

3) Secondary Progressive Multiple Sclerosis (SPMS):
SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

4) Primary Progressive Multiple Sclerosis (PPMS):
PPMS is characterized by a steady progression of increasing neurological deficits without distinct attacks or remissions. Cerebral lesions, diffuse spinal cord damage and evidence of axonal loss are evident on the MRI of patients with PPMS.

5) Progressive-Relapsing Multiple Sclerosis (PRMS):
PRMS has periods of acute exacerbations while proceeding along a course of increasing neurological deficits without remissions. Lesions are evident on MRI of patients suffering from PRMS (Multiple sclerosis: its diagnosis, symptoms, types and stages, 2003, albany.net.about.tjc/multiple-sclerosis.html; What are the Types of Multiple Sclerosis?, 2005, <imaginis.com/multiple-sclerosis/types-of-ms.asp-?mode=1).

Chronic progressive multiple sclerosis is a term used to collectively refer to SPMS, PPMS, and PRMS (Types of Multiple Sclerosis (MS), 2005, <themcfox.com/multiple-sclerosis/types-of-ms/types-of-multi-ple-sclerosis.htm>). The relapsing forms of multiple sclerosis are SPMS with superimposed relapses, RRMS and PRMS.

Glatiramer acetate (GA), a mixture of polypeptides which do not all have the same amino acid sequence, is marketed under the tradename Copaxone®. GA comprises the acetate salts of polypeptides containing L-glutamic acid, L-alanine, L-tyrosine and L-lysine at average molar fractions of 0.141, 0.427, 0.095 and 0.338, respectively. The average molecular weight of Copaxone® is between 5,000 and 9,000 daltons. ("Copaxone", Physician's Desk Reference, (2005), Medical Economics Co., Inc., (Montvale, N.J.), 3115.) Chemically, glatiramer acetate is designated L-glutamic acid polymer with L-alanine, L-lysine, L-tyrosine, acetate (salt).

Its structural formula is:
(Glu,Ala,Lys,Tyr)x.X CH$_3$COOH
(C$_5$H$_9$NO$_4$.C$_6$H$_{14}$N$_2$O$_2$.C$_9$H$_{11}$NO$_3$) x.x CHO
CAS-147245-92-9

Copaxone® ("Copaxone", Full Prescribing Information, (February, 2009), FDA Marketing. Label) (20 mg glatiramer acetate daily injection) is an approved therapy for patients with relapsing remitting multiple sclerosis (RRMS), including patients who have experienced a first clinical episode and have MRI features consistent with multiple sclerosis.

GA has also been disclosed for use in the treatment of other autoimmune diseases (U.S. Patent Publication No. 2002/0055466 A1 (R. Aharoni at al.), inflammatory non-autoimmune diseases (U.S. Patent Publication No. 2005/0014694 A1 (V. Wee Yong et al.); and U.S. Patent Application No. 2002/0077278 A1, published Jun. 20, 2002 (Young et al.)) and other diseases (U.S. Patent Publication Nos. 2003/0004099 A1 and 2002/0037848 A1 (Eisenbach-Schwartz, et al.); U.S. Pat. No. 6,514,938 B1, issued Feb. 4, 2003 (Gad et al.); PCT International Publication No. WO 01/60392, published Aug. 23, 2001 (Gilbert at al.); PCT International. Publication No. WO 00/27417, published May 19, 2000 (Aharoni et al.); and PCT International Publication No. WO 01/97846, published Dec. 27, 2001 (Moses at al.).

The 20 mg/day subcutaneous (s.c.) dose has been shown to reduce the total number of enhancing lesions in MS patients as measured by MRI (G. Comi et al., European/Canadian Multicenter, Double-Blind, Randomized, Placebo-Controlled Study of the Effects of Glatiramer Acetere on Magnetic Resonance Imaging-Measured Disease Activity and Burden in Patients with Relapsing Multiple Sclerosis, Ann. Neurol. 49:290-297 (2001)).

Safety data accumulated for GA in clinical trials shows that the drug product is safe and well tolerated.

Disclosed is an effective low frequency dosage regimen of GA administration to patients suffering from a relapsing form of multiple sclerosis, including patients who have experienced a first clinical episode and have MRI features consistent with multiple sclerosis.

SUMMARY OF THE INVENTION

This invention provides a method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

This invention also provides a method of increasing the tolerability of GA treatment in a human patient suffering from relapsing-remitting multiple sclerosis or a patient who has experienced a first clinical episode and is determined to be at high risk of developing clinically definite multiple sclerosis which comprises reducing the frequency of subcutaneous injections of a pharmaceutical composition comprising a therapeutically effective dose of glatiramer acetate to three times over a period of seven days with at least one day between every injection.

In another embodiment, the therapeutically effective dose of glatiramer acetate is 40 mg/ml.

This invention also provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention additionally provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention yet also provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention further provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention provides glatiramer acetate for use in treating relapsing-remitting multiple sclerosis in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

This invention also provides glatiramer acetate for use in increasing the tolerability of GA treatment in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

DETAILED DESCRIPTION OF THE INVENTION

This invention provides a method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

In another embodiment, there are three injections for every seven days and there must be at least one day between each injection. In a further embodiment, possible injection schedules include Day 1, Day 3, Day 5; Day 1, Day 3, Day 6; Day 1, Day 3, Day 7; Day 1, Day 4, Day 6; Day 1, Day 4, Day 7; Day 1, Day 5, Day 7; Day 2, Day 4, Day 6; Day 2, Day 4, Day 7; Day 2, Day 5, Day 7; or Day 3, Day 5, Day 7.

In an embodiment, alleviating a symptom comprises reducing the frequency of relapses.

In yet another embodiment, alleviating a symptom comprises reducing the mean cumulative number of Gd-enhancing lesions in the brain of the patient.

In another embodiment, alleviating a symptom comprises reducing the mean number of new $T_2$ lesions in the brain of the patient.

In a further embodiment, alleviating a symptom comprises reducing the cumulative number of enhancing lesions on $T_1$-weighted images in the patient.

In another embodiment, alleviating a symptom comprises reducing brain atrophy in the patient.

In another embodiment, alleviating a symptom comprises increasing the time to a confirmed relapse in the patient.

In another embodiment, alleviating a symptom comprises reducing the total number of confirmed relapses in the patient.

In another embodiment, alleviating a symptom comprises reducing the progression of MRI-monitored disease activity in the patient.

In another embodiment, alleviating a symptom comprises reducing total volume of $T_2$ lesions in the patient.

In another embodiment, alleviating a symptom comprises reducing the number of new hypointense lesions on enhanced $T_1$ scans in the patient.

In another embodiment, alleviating a symptom comprises reducing the total volume of hypointense lesions on enhanced $T_1$ scans in the patient.

In another embodiment, alleviating a symptom comprises reducing the level of disability as measured by EDSS Score in the patient.

In another embodiment, alleviating a symptom comprises reducing the change in EDSS Score in the patient.

In another embodiment, alleviating a symptom comprises reducing the change in Ambulation Index in the patient.

In another embodiment, alleviating a symptom comprises reducing the level of disability as measured by EuroQoL (EQ5D) questionnaire in the patient.

In another embodiment, alleviating a symptom comprises reducing the level of disability as measured by the work productivity and activities impairment-General Health (WPAI-GH) questionnaire in the patient.

In an additional embodiment, the pharmaceutical composition is in a prefilled syringe for self administration by the patient.

In yet another embodiment, the therapeutically effective dose 2D of glatiramer acetate is 40 mg/ml. In a further embodiment, the therapeutically effective dose of glatiramer acetate is 40 mg/0.75 ml.

In a further embodiment, the patient has not received glatiramer acetate therapy prior to initiation of the subcutaneous injections.

In an embodiment, the pharmaceutical composition is in the form of a sterile solution.

In another embodiment, the pharmaceutical composition further comprises mannitol.

In yet another embodiment, the pharmaceutical composition has a pH in the range of 5.5 to 8.5.

In an embodiment, the pharmaceutical composition has a pH in the range of 5.5 to 7.0.

In an embodiment the frequency of an immediate post injection reaction or the frequency of an injection site reaction is reduced relative to daily subcutaneous administration of 20 mg glatiramer acetate.

This invention also provides a method of increasing the tolerability of GA treatment in a human patient suffering from relapsing-remitting multiple sclerosis or a patient who has experienced a first clinical episode and is determined to be at high risk of developing clinically definite multiple sclerosis which comprises reducing the frequency of subcutaneous injections of a pharmaceutical composition comprising a therapeutically effective dose of glatiramer acetate to three times over a period of seven days with at least one day between every injection.

In another embodiment, increasing the tolerability of GA treatment in the human patient suffering from a relapsing form of multiple sclerosis comprises reducing the frequency of an immediate post injection reaction.

In yet another embodiment, the immediate post injection reaction is palpitations, feeling hot, flushing, hot flushes, tachycardia, dyspnoea, chest discomfort, chest pain, non-cardiac chest, asthenia, back pain, bacterial infection, chills, cyst, face edema, fever, flu syndrome, infection, injection site erythema, injection site hemorrhage, injection site induration, injection site inflammation, injection site mass, injection site pain, injection site pruritus, injection site urticaria, injection site welt, neck pain, pain, migraine, syncope, tachycardia, vasodilatation, anorexia, diarrhea, gastroenteritis, gastrointestinal disorder, nausea, vomiting, ecchymosis, peripheral edema, arthralgia, agitation, anxiety, confusion, foot drop, hypertonia, nervousness, nystagmus, speech disorder, tremor, vertigo, bronchitis, dyspnea, laryngismus, rhinitis, erythema, herpes simplex, pruritus, rash, skin nodule, sweating, urticaria, ear pain, eye disorder, dysmenorrheal, urinary urgency, or vaginal moniliasis.

In an additional embodiment, increasing the tolerability of GA treatment in the human patient suffering from a relapsing form of multiple sclerosis comprises reducing the frequency of an injection site reaction.

In a further embodiment, the injection site reaction is erythema, hemorrhage, induration, inflammation, mass, pain, pruritus, urticaria, or welt that occurs immediately around the site of injection.

In an embodiment, a single clinical attack includes a clinical episode of optic neuritis, blurring of vision, diplopia, involuntary rapid eye movement, blindness, loss of balance, tremors, ataxia, vertigo, clumsiness of a limb, lack of coordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

In another embodiment, prior to administration the patient has at least 1 cerebral lesion detectable by an MRI scan and suggestive of multiple sclerosis.

In yet another embodiment, the lesion is associated with brain tissue inflammation, myelin sheath damage or axonal damage.

In an additional embodiment, the lesion is a demyelinating white matter lesion visible on brain MRI.

In a further embodiment, the white matter lesions are at least 3 mm in diameter.

This invention also provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention additionally provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention yet also provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention further provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention provides glatiramer acetate for use in treating relapsing-remitting multiple sclerosis in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

This invention also provides glatiramer acetate for use in increasing the tolerability of GA treatment in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

DEFINITIONS

As used herein, immediate post injection reaction (IRPR) refers to a reaction such as, palpitations, feeling hot, flushing, hot flushes, tachycardia, dyspnoea, chest discomfort, chest pain, and non-cardiac chest pain that occurs immediately following injection. Reactions may also include asthenia, back pain, bacterial infection, chills, cyst, face edema, fever, flu syndrome, infection, injection site erythema, injection site hemorrhage, injection site induration, injection site inflammation, injection site mass, injection site pain, injection site pruritus, injection site urticaria, injection site welt, neck pain, pain, migraine, syncope, tachycardia, vasodilatation, anorexia, diarrhea, gastroenteritis, gastrointestinal disorder, nausea, vomiting, ecchymosis, peripheral edema, arthralgia, agitation, anxiety, confusion, foot drop, hypertonia, nervousness, nystagmus, speech disorder, tremor, vertigo, bronchitis, dyspnea, laryngismus, rhinitis, erythema, herpes simplex, pruritus, rash, skin nodule, sweating, urticaria, ear pain, eye disorder, dysmenorrheal, urinary urgency, and vaginal moniliasis.

As used herein, injection site reaction (ISR) refers to a reaction such as erythema, hemorrhage, induration, inflammation, mass, pain, pruritus, urticaria, and welt that Occurs immediately around the site of injection.

As used herein, "tolerability" relates to the level of discomfort associated with GA treatment. Tolerability is associated with the frequency and severity of post injection reactions and injection site reactions. Tolerability influences the period that a patient can follow GA treatment.

As used herein, the term Gd-enhancing lesions, refers to lesions that result from a breakdown of the blood-brain barrier, which appear in contrast studies using gandolinium contrast agents. Gandolinium enhancement provides information as to the age of a lesion, as Gd-enhancing lesions typically occur within a six week period of lesion formation.

As used herein, the term $T_1$-weighted MRI images refers to an MR-image that emphasizes $T_1$ contrast by which lesions may be visualized. Abnormal areas in a $T_1$-weighted MRI image are "hypointense" and appear as dark spots. These spots are generally older lesions.

As used herein, the term $T_2$-weighted MRI image, refers to an MR-image that emphasizes $T_2$ contrast by which lesions may be visualized. $T_2$ lesions represent new inflammatory activity.

As used herein, the term "unit dosage" refers to physically discrete units suited as single administration dose for a subject to be treated, containing a therapeutically effective quantity of active compound in association with the required pharmaceutical carrier, e.g., a syringe.

As used herein, clinically isolated syndrome (CIS) refers to 1) a single clinical attack suggestive of MS and 2) at least one lesion suggestive of MS. As an example, the patient has at least 1 cerebral lesion detectable by an MRI scan and suggestive of multiple sclerosis. As an additional example the lesion is associated with brain tissue inflammation, myelin sheath damage or axonal damage. As another example the lesion is a demyelinating white matter lesion visible on brain MRI. In a further example, the white matter lesions are at least 3 mm in diameter.

The term "single clinical attack" is used synonymously with "first clinical episode", "first clinical attack", and "first clinical event" which, for example, presents as a clinical episode of optic neuritis, blurring of vision, diplopia, involuntary rapid eye movement, blindness, loss of balance, tremors, ataxia, vertigo, clumsiness of a limb, lack of coordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

As used herein, the criteria, as defined by Poser et al. Neurology, March 1983, 13 (3): 227-230, used to determine if a subject meets the condition consistent with clinically definite multiple sclerosis (CDMS) are:

Two attacks and clinical evidence of two separate lesions or

Two attacks; clinical evidence of one lesion and paraclinical evidence of another separate lesion.

An attack (also referred to as an exacerbation, flare, or relapse,) is defined clinically as the sudden appearance or worsening of a symptom or symptoms of neurological dysfunction, with or without objective confirmation.

Clinical evidence of a lesion is defined as signs of neurological dysfunction demonstrable by neurological examination. An abnormal sign constitutes clinical evidence even if no longer present, but was recorded in the past by a competent examiner.

Paraclinical evidence of a lesion is defined as the demonstration by means of various tests and procedures of the existence of a lesion of the CNS that has not produced clinical signs but that may or may not have caused symptoms in the past. Such evidence may be derived from the hot-bath test, evoked response studies, neuroimaging, and expert neurological assessment. These tests are considered to be extensions of the neurological examination and not laboratory procedures.

As used herein, the term "glatiramoid" refers a complex mixture of the acetate salts of synthetic polypeptides, non-uniform with respect to molecular weight and sequence.

This invention is illustrated in the Examples section which follows. This section is set forth to aid in an understanding of the invention but is not intended to, and should not be construed to, limit in any way the invention as set forth in the claims which follow thereafter.

EXPERIMENTAL DETAILS

Example 1

A multinational, multicenter, randomized, phase III parallel-group study performed in subjects with Relapsing-Remitting Multiple Sclerosis (RRMS) to assess the efficacy, safety and tolerability of Glatiramer Acetate (GA) injection 40 mg/ml administered three times weekly by subcutaneous injection over placebo in a double-blind design.

Methods:

The study is designed to select three days a week for injection. Three injections are administered for every seven days and there must be at least one day between each injection.

Study Duration:
   Screening phase: 1 month
   Placebo Controlled (PC) Phase: 12 months of 40 mg/ml or matching placebo administered three times weekly by subcutaneous injection.
   Open Label (OL) Extension: All subjects will continue treatment with the GA 40 mg/ml administered three times a week, until this dose is commercially available for the treatment of relapsing remitting multiple sclerosis (RRMS) patients or until the development of this dose for MS is stopped by the Sponsor.
Study Population:
   Subjects with RRMS
Number of Subjects:
   1350 subjects
Study Objective(s):
   To assess the efficacy, safety and tolerability of Glatiramer Acetate (GA) injection 40 mg/ml administered three times weekly compared to placebo in a double-blind study design.
Study Design:
   Eligible subjects are randomized in a 2:1 ratio (40 mg:placebo) and assigned to one of the following three treatment arms:
   1. 40 mg s.c. GA three times weekly (900 subjects)
   2. Matching placebo three times weekly (450 subjects)
   During the PC phase, subjects are evaluated at study sites for a total of 7 scheduled visits at months: −1 (screening), 0 (baseline), 1, 3, 6, 9, and 12 (End of PC phase).
   Subjects successfully completing the study are offered the opportunity to enter into an open label extension in which all subjects will continue treatment with 40 mg/ml GA dose. This is done until the 40 mg/ml GA dose is commercially available for the treatment of relapsing remitting multiple sclerosis (RRMS) patients or until the development of this dose regimen is stopped by the Sponsor.
   The termination visit of the PC phase will serve as the baseline visit of the OL phase. This phase will include scheduled visits every 3 months for the first 12 months, then scheduled visits every 6 months and will be completed with a termination visit.
   During the study, the following assessments are performed (regardless of the treatment assignment) at the specified time points:
   Vital signs are measured at each study visit.
   A physical examination is performed at months −1 (screening), 0 (baseline) 6, 12 (end of PC phase) and every 6 months thereafter. In addition, a physical examination will be performed at the termination visit of the OL phase.
   The following safety clinical laboratory tests are performed:
      Complete blood count (CBC) with differential—at all scheduled visits in the PC phase, and every 12 months thereafter. In addition this test will be performed at the termination visit of the OL phase.
      Serum chemistry (including electrolytes, creatinine, urea and liver enzymes) and urinalysis—at all scheduled visits in the PC phase, and every 12 months thereafter. In addition this test will be performed at the termination visit of the OL phase.
      Serum β-hCG in women of child-bearing potential is performed at months −1 (screening), 0 (baseline), 12 (end of PC phase), and every 12 months thereafter. In addition this test will be performed at the termination visit of the OL phase.
   ECG is performed at months −1 (screening), 0 (baseline), 12 (end of PC phase), and every 12 months thereafter. In addition an ECG will be performed at the termination visit of the OL phase.
   Chest X-ray is performed at month −1 (screening) if not performed within 6 months prior to screening visit.
   Adverse Events (AEs) are monitored throughout the study.
   Concomitant Medications are monitored throughout the study.
   Neurological evaluations, including Neurostatus [Functional Systems (FS), Expanded Disability Status Scale (EDSS), Ambulation Index (AI)] are performed at months −1 (screening), 0 (baseline), 3, 6, 9, 12 (end of PC phase) and every 6 months thereafter. In addition, a neurological examination are performed at the termination visit of the OL phase.
   The general health status is assessed by the EuroQoL (EQ5D) questionnaire at months 0 (baseline) and 12 (end of PC phase).
   Additional quality of life parameters are assessed by the WPAI (Work Productivity and Activities Impairment) Questionnaire at month 0 (baseline), 3, 6, 9 and 12 (end of PC phase).
   All subjects undergo MRI scans at months 0 (13-7 days prior to baseline visit), 6 and 12 (end of PC phase). Following the results of the PC phase, the Sponsor may decide to perform an MRI scan at the termination visit of the OL phase.
   Relapses are confirmed/monitored throughout the study.
Ancillary Studies:
   Blood samples for determination of anti-GA antibodies are collected for all subjects at months 0 (baseline), 1, 3, 6, 9, 12 (end of PC phase), 18 and 24.
   Blood samples for evaluation of PBL proliferation in response to GA, as well as other immunological parameters, are collected in a subset of subjects at months 0 (baseline), 1, 3, 6, and 12 (end of PC phase).
   Blood samples for Pharmacogenetic (PGx) analysis are collected for all subjects twice during the study, preferably at month 0 (baseline) and month 1.
   The allowed treatment for a multiple sclerosis relapse will be intravenous methylprednisolone 1 gr/day for up to 5 consecutive days.
Re-Consent Criteria
   In case of a confirmed diagnosis of MS relapse (as defined in the protocol), or in case of an increase in EDSS of 1.5 points or more, sustained for at least 3 months, during the placebo-controlled phase, the following actions are taken:
   The subject is reminded of the current available MS medications/treatments and the opportunity to terminate the study.
   The subject is requested to re-sign an informed consent form if he/she chooses to continue to participate in the study, in the same treatment assignment.
   The study is closely monitored through the study course by the sponsor's personnel as well as by an external independent data monitoring committee (DMC) in order to ensure subjects' welfare.
Inclusion/Exclusion:
Inclusion Criteria:
   Subjects must have a confirmed and documented MS diagnosis as defined by the Revised McDonald criteria (Ann Neurol 2005: 58:840-846), with a relapsing-remitting disease course.
   Subjects must be ambulatory with an EDSS score of 0-5.5 in both screening and baseline visits.

Subjects must be in a relapse-free, stable neurological condition and free of corticosteroid treatment [intravenous (IV), intramuscular (IM) and/or per os (PO)] or ACTH 30 days prior to screening (month −1) and between screening (month −1) and baseline (month 0) visits.

Subjects must have had experienced one of the following:
At least one documented relapse in the 12 months prior to screening, or
At least two documented relapses in the 24 months prior to screening, or
One documented relapse between 12 and 24 months prior to screening with at least one documented $T_1$-Gd enhancing lesion in an MRI performed within 12 months prior to screening.

Subjects must be between 18 and 55 years of age, inclusive.

Women of child-bearing potential must practice an acceptable method of birth control [acceptable methods of birth control in this study include: surgical sterilization, intrauterine devices, oral contraceptive, contraceptive patch, long-acting injectable contraceptive, partner's vasectomy or a double-barrier method (condom or diaphragm with spermicide)].

Subjects must be able to sign and date a written informed consent prior to entering the study.

Subjects must be willing and able to comply with the protocol requirements for the duration of the study.

Exclusion Criteria:
Subjects with progressive forms of MS.
Use of experimental or investigational drugs, and/or participation in drug clinical studies within the 6 months prior to screening.
Use of immunosuppressive (including Mitoxantrone (Novantrone®) or cytotoxic agents within 6 months prior to the screening visit.
Previous use of either natalizumab (Tysabri®) or any other monoclonal antibodies within 2 years prior to screening.
Use of cladribine within 2 years prior to screening.
Previous treatment with immunomodulators (including IFNβ 1a and 1b, and IV Immunoglobulin (IVIg) within 2 months prior to screening.
Previous use of GA or any other glatiramoid.
Chronic (more than 30 consecutive days) systemic (IV, PO or IM) corticosteroid treatment within 6 months prior to screening visit.
Previous total body irradiation or total lymphoid irradiation.
Previous stem-cell treatment, autologous bone marrow transplantation or allogenic bone marrow transplantation.
Known human immunodeficiency virus (HIV) positive status.
Pregnancy or breastfeeding.
Subjects with a clinically significant or unstable medical or surgical condition that would preclude safe and complete study participation, as determined by medical history, physical exams, ECG, abnormal laboratory tests and chest X-ray. Such conditions may include hepatic, renal or metabolic diseases, systemic disease, acute infection, current malignancy or recent history (5 years) of malignancy, major psychiatric disorder, history of drug and/or alcohol, abuse and allergies that could be detrimental according to the investigator's judgment.
A known history of sensitivity to Gadolinium.
Inability to successfully undergo MRI scanning.
A known drug hypersensitivity to mannitol.

Route and Dosage Form:
Glatiramer Acetate 40 mg in 1 ml for subcutaneous injection in a pre-filled syringe (PFS), administered three times a week.
Matching placebo injection (mannitol in 1 ml WFI) for subcutaneous injection in a pre-filled syringe (PFS).

Outcome Measures:
Primary Outcome Measure:
The total number of confirmed relapses during the 12 month PC phase.
Secondary Outcome Measure:
The number of new $T_2$ lesions at month 12 (end of PC phase) as compared to baseline scan.
The cumulative number of enhancing lesions on $T_1$-weighted images taken at months 6 and 12 (end of PC phase).
Brain atrophy as defined by the percent brain volume change from baseline to month 12 (end of PC phase).

Exploratory Endpoints:
The following assessments are presented in an exploratory manner.
The time to the first confirmed relapse during the placebo-controlled phase.
The proportion of relapse-free subjects during the placebo-controlled phase.
The total number of confirmed relapses during the placebo-controlled phase requiring hospitalization and/or IV steroids.
The proportion (%) of subjects with confirmed EDSS progression during the placebo-controlled phase (progression of at least 1 EDSS point sustained for at least 3 months).
Change from baseline to month 12 (end of placebo-controlled phase) in EDSS Score.
Change from baseline to month 12 (end of placebo-controlled phase) in Ambulation Index.
The total volume of $T_2$ lesions at month 12 (end of placebo-controlled phase)
The number of new hypointense lesions on enhanced $T_1$ scans at month 12 (end of placebo-controlled phase) as compared to the baseline scan.
The total volume of hypointense lesions on enhanced $T_1$ scans at month 12 (end of placebo-controlled phase).
Brain atrophy as defined by the percentage change from baseline to month 12 (end of placebo-controlled phase) in normalized gray matter volume and in normalized white matter volume.
The general health status, as assessed by the EuroQoL (EQ5D) questionnaire.
Assessment of the effect of general health and symptom severity on work, using the work productivity and activities impairment General Health (WPAI-GH) questionnaire.

Safety and Tolerability Outcome Measures:
Safety:
Adverse events
Vital signs
ECG findings
Clinical laboratory parameters
Tolerability:
Proportion of subjects (%) who prematurely discontinued from the study, reason of discontinuation and the time to withdrawal.
Proportion of subjects (%) who prematurely discontinued from the study due to AEs and the time to withdrawal.

Statistical Considerations:

The sample size considerations for the study are based on the following assumptions:

An individual subject's number of confirmed relapses during a one year period reflects a Poisson process with an individual rate of $\lambda i$, and this individual subject rates $\lambda i$ are exponentially distributed with mean $1/\theta$, where $\theta$ is the population's annualized relapse rate. This approach models the total number of confirmed relapses as an Over Dispersed Poisson distribution.

The expected annualized relapse rate in an untreated subject population is $\theta=0.35$ relapses per year.

Treatment with 40 mg s.c. GA three times weekly reduces the subject population annualized relapse rate by 30% or more when compared to the placebo group. That is, the expected annualized relapse rate of the GA treated populations is $\theta=0.245$ relapses per year or less.

In addition, the following are also incorporated in the sample size calculation:

15% of the subjects drop out during the treatment duration. This drop out rate is taken into account in the calculations, as on the average, a subject who drops out of the study contributes 6 months of exposure to the treatment Hochberg's step-up modification to Bonferroni's method is used to maintain the experiment-wise type-I error when comparing multiple treatment arms to placebo, and the p-values for the IAs are calculated using the O'brien-Fleming alpha spending functions.

A simulation study accounting for the above underlying assumptions used the Quasi-Likelihood (over-dispersed) Poisson Regression (SAS® PROC GENMOD), revealed that a total of 1350 subjects (900 subjects in the 40 mg GA arm, and 450 subjects to the placebo arm) provide approximately 90% power to detect a significant difference in the total number of confirmed relapses as described above.

The analysis of the total numbers of confirmed relapses during the study period is based on baseline adjusted Quasi-Likelihood (over-dispersed) Poisson Regression.

The analysis of the number of new $T_2$ lesions at month 12 and of the cumulative number of enhancing lesions on $T_1$-weighted images taken at months 6 and 12 is based on baseline-adjusted Negative Binomial Regression.

The analysis of Brain Atrophy will be based on Analysis of Covariance (ANCOVA).

Results

Primary Outcome Measure:

Treatment with 40 mg s.c. GA three times weekly reduces the subject population annualized relapse rate by 30% or more when compared to the placebo group. Treatment with 40 mg s.c. GA three times weekly is at least as effective as 20 mg s.c. GA daily administration at reducing the subject population annualized relapse rate.

Secondary Outcome Measures:

Treatment with 40 mg s.c. GA three times weekly significantly reduces the number of new $T_2$ lesions at month 12. Treatment with 40 mg s.c. GA three times weekly is at least as effective as 20 mg s.c. GA daily administration at reducing the number of new $T_2$ lesions at month 12.

Treatment with 40 mg s.c. GA three times weekly significantly reduces the cumulative number of enhancing lesions on $T_1$-weighted images taken at months 6 and 12. Treatment with 40 mg s.c. GA three times weekly is at least as effective as 20 mg s.c. GA daily administration at reducing the cumulative number of enhancing lesions on $T_1$-weighted images taken at months 6 and 12.

Treatment with 40 mg s.c. GA three times weekly significantly reduces brain atrophy as defined by the percent brain volume change from baseline to month 12. Treatment with 40 mg s.c. GA three times weekly is at least as effective as 20 mg s.c. GA daily administration at reducing brain atrophy as defined by the percent brain volume change from baseline to month 12.

Exploratory Endpoints:

Treatment with 40 mg s.c. GA three times weekly significantly increases the time to the first confirmed relapse during the placebo-controlled phase. Treatment with 40 mg s.c. GA three times weekly is at least as effective as 20 mg s.c. GA daily administration at increasing the time to the first confirmed relapse during the placebo-controlled phase.

Treatment with 40 mg s.c. GA three times weekly significantly increases the proportion of relapse-free subjects during the placebo-controlled phase. Treatment with 40 mg s.c. GA three times weekly is at least as effective as 20 mg s.c. GA daily administration at increasing the proportion of relapse-free subjects during the placebo-controlled phase.

Treatment with 40 mg s.c. GA three times weekly significantly increases the proportion of relapse-free subjects during the placebo-controlled phase. Treatment with 40 mg s.c. GA three times weekly is at least as effective as 20 mg s.c. GA daily administration at increasing the proportion of relapse-free subjects during the placebo-controlled phase.

Treatment with 40 mg s.c. GA three times weekly significantly reduces the total number of confirmed relapses during the placebo-controlled phase requiring hospitalization and/or IV steroids. Treatment with 40 mg s.c. GA three times weekly is at least as effective as 20 mg s.c. GA daily administration at reducing the total number of confirmed relapses during the placebo-controlled phase requiring hospitalization and/or IV steroids.

Treatment with 40 mg s.c. GA three times weekly significantly reduces the progression of MRI-monitored disease activity in the patient. Treatment with 40 mg s.c. GA three times weekly is at least as effective as 20 mg s.c. GA daily administration at reducing the progression of MRI-monitored disease activity in the patient.

Treatment with 40 mg s.c. GA three times weekly significantly reduces the total volume of $T_2$ lesions at month 12. Treatment with 40 mg s.c. GA three times weekly is at least as effective as 20 mg s.c. GA daily administration at reducing total volume of $T_2$ lesions at month 12.

Treatment with 40 mg s.c. GA three times weekly significantly reduces the number of new hypointense lesions on enhanced $T_1$ scans at month 12 as compared to the baseline scan. Treatment with 40 mg s.c. GA three times weekly is at least as effective as 20 mg s.c. GA daily administration at reducing the number of new hypointense lesions on enhanced $T_1$ scans at month 12 as compared to the baseline scan.

Treatment with 40 mg s.c. GA three times weekly significantly reduces the total volume of hypointense lesions on enhanced $T_1$ scans at month 12. Treatment with 40 mg s.c. GA three times weekly is at least as effective as 20 mg s.c. GA daily administration at reducing the total volume of hypointense lesions on enhanced $T_1$ scans at month 12.

Treatment with 40 mg s.c. GA three times weekly significantly reduces brain atrophy as defined by the percentage change from baseline to month 12 in normalized gray matter volume and in normalized white matter volume. Treatment with 40 mg s.c. GA three times weekly is at least as effective as 20 mg s.c. GA daily administration at reducing brain atrophy as defined by the percentage change from baseline to month 12 in normalized gray matter volume and in normalized white matter volume.

Treatment with 40 mg s.c. GA three times weekly significantly reduces the level of disability as measured by EDSS Score. Treatment with 40 mg s.c. GA three times weekly is at least as effective as 20 mg s.c. GA daily administration at reducing the level of disability as measured by EDSS Score.

Treatment with 40 mg s.c. GA three times weekly significantly reduces the proportion (%) of subjects with confirmed EDSS progression during the placebo-controlled phase (progression of at least 1 EDSS point sustained for at least 3 months). Treatment with 40 mg s.c. GA three times weekly is at least as effective as 20 mg s.c. GA daily administration at reducing proportion (%) of subjects with confirmed EDSS progression during the placebo-controlled phase, (progression of at least 1 EDSS point sustained for at least 3 months).

Treatment with 40 mg s.c. GA three times weekly significantly reduces the change from baseline to month 12 (end of placebo-controlled phase) in EDSS Score. Treatment with 40 mg s.c. GA three times weekly is at least as effective as 20 mg s.c. GA daily administration at reducing the change from baseline to month 12 (end of placebo-controlled phase) in EDSS Score.

Treatment with 40 mg s.c. GA three times weekly significantly reduces the change from baseline to month 12 (end of placebo-controlled phase) in Ambulation Index. Treatment with 40 mg s.c. GA three times weekly is at least as effective as 20 mg s.c. GA daily administration at reducing the change from baseline to month 12 (end of placebo-controlled phase) in Ambulation Index.

Treatment with 40 mg s.c. GA three times weekly significantly reduces the level of disability as measured by EuroQoL (EQ5D) questionnaire. Treatment with 40 mg s.c. GA three times weekly is at least as effective as 20 mg s.c. GA daily administration at reducing the level of disability as measured by EuroQoL (EQ5D) questionnaire.

Treatment with 40 mg s.c. GA three times weekly significantly reduces the level of disability as measured by the work productivity and activities impairment-General Health (WPAI-GH) questionnaire. Treatment with 40 mg s.c. GA three times weekly is at least as effective as 20 mg s.c. GA daily administration at reducing the level of disability as measured by the work productivity and activities impairment-General Health (WPAI-GH) questionnaire.

Discussion

A significant drawback to GA therapy is the requirement of daily injections, which can be inconvenient. Moreover, in all clinical trials, injection-site reactions were seen to be the most frequent adverse reactions and were reported by the majority of patients receiving GA. In controlled studies, the proportion of patients reporting these reactions, at least once, was higher following treatment with GA (70%) than placebo injections (37%). The most commonly reported injection-site reactions, which were more frequently reported in GA vs. placebo-treated patients, were erythema, pain, mass, puritus, edema, inflammation and hypersensitivity.

However, several obstacles and limitations with potential approaches for addressing the drawbacks exist to current GA therapy. Subcutaneous drug delivery is limited, firstly, by the acceptable injection volume. Typically no more than 1 to 2 ml of solution is permitted (Kansara V, Mitre A, Wu Y, Subcutaneous Delivery. Drug Deliv Technol, June 2009; 9(6):38-42). Secondly, the potential exists for drug degradation at the site of injection resulting in reduced bioavailability. Thirdly, based on the physiochemical properties of the drug, potent compounds may become locally trapped in the interstitial space which can lead to further localized irritation, precipitation of the drug and concentration-dependent adverse effects (Kansara V, Mitra A, Wu Y, Subcutaneous Delivery. Drug Deliv Technol, June 2009; 9(6):38-42). Finally, due to the complex pharmacokinetic behavior of a drug, variation in the frequency of administration is unpredictable and requires empirical testing. For example, although controlled clinical trials have demonstrated the efficacy of IFNβ-1b in the treatment of MS, patient compliance, efficacy and tolerability are affected by the dosage regimen used. Merely increasing the dose of IFNβ-1b is insufficient to increase efficacy, the frequency of administration must also be increased (Luca Durelli, J Neurol (2003) 250 [Suppl 4]).

Accordingly, the subject application discloses an effective low frequency dosage regimen of GA administration to patients suffering from a relapsing form of multiple sclerosis, including patients who have experienced a first clinical episode and have MRI features consistent with multiple sclerosis. Based on the performance of the dosage regimen in these studies, the administration of three s.c. injections over a period of seven days with at least one day between every injection is also expected to work in the treatment of patients who have experienced a clinically isolated syndrome (CIS). This is based on the fact that the 20 mg daily s.c. injection has been shown to work in PCT International Application No. PCT/US2008/013146 (see International Publication No. WO 2009/070298 and also U.S. Patent Application Publication No. US 2009-0149541 A1).

What is claimed is:

1. A method of treatment of a human patient suffering from a relapsing form of multiple sclerosis comprising administration to the human patient of three subcutaneous injections of a 40 mg/ml dose of glatiramer acetate per week so as to treat the human patient.

2. The method of claim 1, wherein the human patient is suffering from relapsing-remitting multiple sclerosis.

3. The method of claim 1, wherein the human patient has experienced a first clinical episode and has MRI features consistent with multiple sclerosis.

4. The method of claim 2, wherein the three subcutaneous injections are on three days each week selected from the group consisting of day 1, day 3 and day 5; day 1, day 3 and day 6; day 1, day 4 and day 6; day 2, day 4 and day 6; day 2, day 4 and day 7; 2, day 5 and day 7; and day 3, day 5 and day 7.

5. The method of claim 3, wherein the three subcutaneous injections are on three days every week selected from the group consisting of day 1, day 3 and day 5; day 1, day 3 and day 6; day 1, day 4 and day 6; day 2, day 4 and day 6; day 2, day 4 and day 7; 2, day 5 and day 7; and day 3, day 5 and day 7.

6. The method of claim 2, wherein the glatiramer acetate is present in 1 ml of a pharmaceutical composition in a prefilled syringe for self administration by the human patient.

7. The method of claim 3, wherein the glatiramer acetate is present in 1 ml of a pharmaceutical composition in a prefilled syringe for self administration by the human patient.

8. The method of claim 6, wherein the pharmaceutical composition further comprises mannitol and has a pH in the range of 5.5 to 7.0.

9. The method of claim 7, wherein the pharmaceutical composition further comprises mannitol and has a pH in the range of 5.5 to 7.0.

10. A method of treatment of a human patient suffering from a relapsing form of multiple sclerosis comprising subcutaneous injection by the human patient of a 40 mg/ml dose of glatiramer acetate three times per week with at least one day between every subcutaneous injection, wherein the glatiramer acetate is present in 1 ml of a pharmaceutical composition in a prefilled syringe for self injection by the human patient, and wherein the pharmaceutical composition further comprises mannitol and has a pH in the range of 5.5 to 7.0.

11. The method of claim 10, wherein each subcutaneous injection is on day 1, day 3 and day 5; day 1, day 3 and day 6; day 1, day 4 and day 6; day 2, day 4 and day 6; day 2, day 4 and day 7; 2, day 5 and day 7; or day 3, day 5 and day 7 every week.

12. The method of claim 10, wherein the human patient is suffering from relapsing-remitting multiple sclerosis.

\* \* \* \* \*